United States Patent [19]

November et al.

[11] 4,349,881
[45] Sep. 14, 1982

[54] VIBRATION INSTRUMENTS

[75] Inventors: Milton H. November, Hacienda Heights; LaVern D. Lyon, Claremont; Joseph J. Ponzi, Alhambra, all of Calif.

[73] Assignee: International Telephone and Telegraph Corporation, New York, N.Y.

[21] Appl. No.: 168,709

[22] Filed: Jul. 14, 1980

[51] Int. Cl.³ .............................................. G01F 1/00
[52] U.S. Cl. .................................. 364/509; 73/32 A; 364/556
[58] Field of Search ................ 364/508, 509, 556–558; 73/32 A, 339 A

[56] References Cited

U.S. PATENT DOCUMENTS

| | | | |
|---|---|---|---|
| 3,878,374 | 4/1975 | Schlatter | 364/508 X |
| 3,885,140 | 5/1975 | Schlatter | 364/558 X |
| 3,902,365 | 9/1975 | Knauth | 73/32 A X |
| 3,934,127 | 1/1976 | Schlatter et al. | 364/558 X |
| 4,020,330 | 4/1977 | Bae | 364/558 |
| 4,132,110 | 1/1979 | Muramoto | 73/32 A |
| 4,184,205 | 1/1980 | Morrow | 364/508 |
| 4,282,742 | 8/1981 | Kalotay et al. | 73/32 A |

FOREIGN PATENT DOCUMENTS

| | | |
|---|---|---|
| 1095257 | 12/1967 | United Kingdom . |
| 1143050 | 2/1969 | United Kingdom . |
| 1254665 | 11/1971 | United Kingdom . |
| 1326729 | 8/1973 | United Kingdom . |
| 1349255 | 4/1974 | United Kingdom . |
| 1446318 | 8/1976 | United Kingdom . |
| 1515668 | 6/1978 | United Kingdom ................ 374/117 |
| 189178 | 9/1975 | U.S.S.R. ............................. 374/117 |

*Primary Examiner*—Edward J. Wise
*Attorney, Agent, or Firm*—A. Donald Stolzy

[57] ABSTRACT

A quartz tuning fork is provided which may be employed in several instruments for measuring the properties of fluids. The tuning fork may be employed, for example, in a gravitometer, a barometer, an altimeter or a temperature sensor.

17 Claims, 14 Drawing Figures

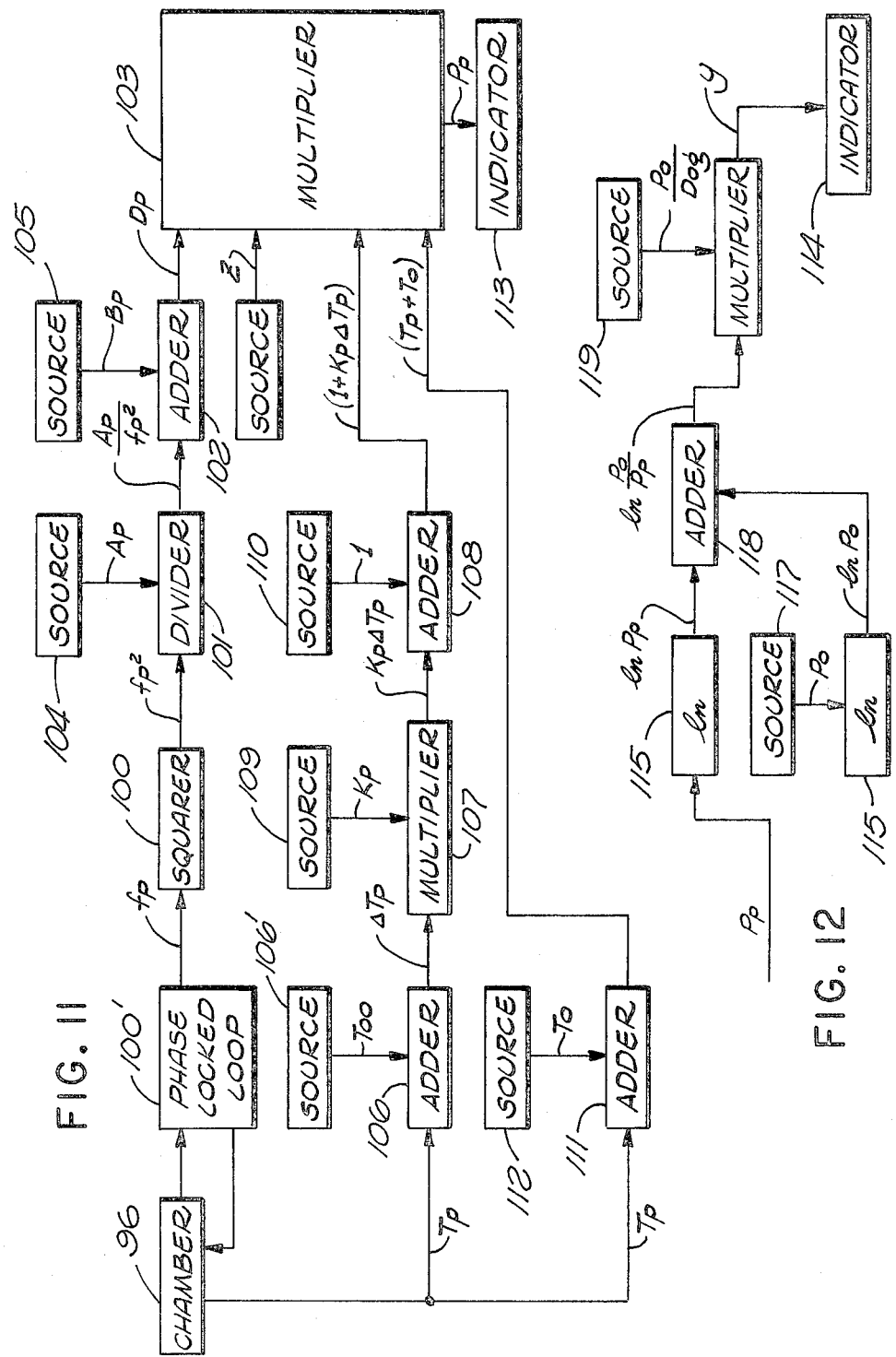

4,349,881

VIBRATION INSTRUMENTS

BACKGROUND OF THE INVENTION

This invention relates to devices employing vibrating members, and more particularly to a vibration instrument for producing an output signal proportional to fluid density and/or for use in the computation of a fluid property.

PRIOR ART STATEMENT

Vibration gravitometers are known in the art. For example, see U.S. Pat. No. 3,934,127 issued Jan. 20, 1976.

Vibration instruments used in the fluid measurement field such as in gravitometry demonstrate a low accuracy and a low degree of stability, repeatability, linearity and resolution.

SUMMARY OF THE INVENTION

In accordance with the vibration instrument of the present invention, the above-described and other disadvantages of the prior art are overcome by providing tuning fork means as a component in a closed loop electromechanical oscillator.

The invention demonstrates a high accuracy and a high degree of stability, repeatability, linearity and resolution.

The accuracy of the present invention will be found to be two or three times better than that of the prior art (e.g. better 0.2 percent reading—95 percent confidence level).

BRIEF DESCRIPTION OF THE DRAWINGS

In the accompanying drawings which illustrate exemplary embodiments of the present invention:

FIG. 11 is a barometer computer constructed in accordance with the present invention;

FIG. 12 is a block diagram of an altimeter computer for use with that shown in FIG. 11;

DESCRIPTION OF THE PREFERRED EMBODIMENTS

Figure 1:
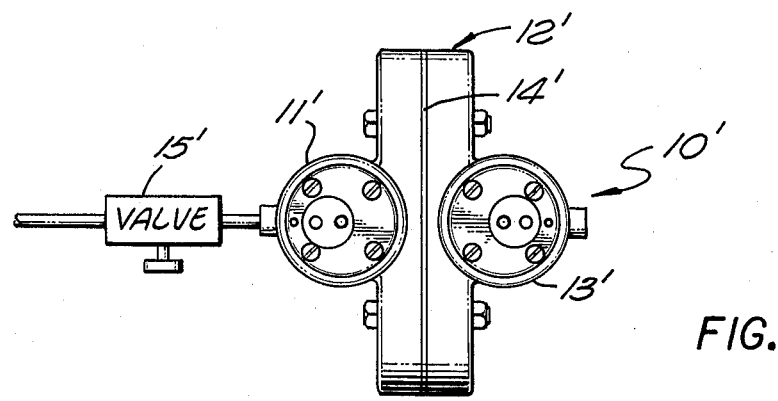
FIG. 1 is a top plan view of a gravitometer constructed in accordance with the present invention.

In FIG. 1, a gravitometer is illustrated at 10' having hollow cylinders 11', 12' and 13'. Cylinder 12' is divided in half by an elastomeric diaphragm 14'.

Figure 2:
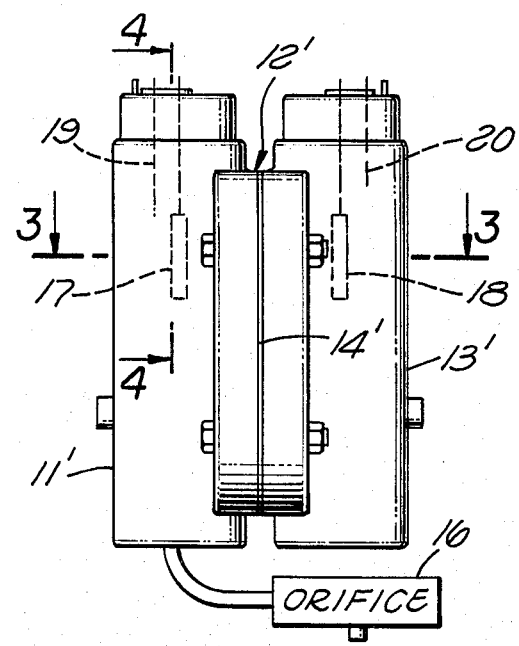
FIG. 2 is a side elevational view of the gravitometer shown in FIG. 1.

A gas of interest is admitted through a needle valve 15' and vented through an orifice 16 (see FIG. 2).

The chamber on the other side of diaphragm 14' is charged with air.

Figure 3:
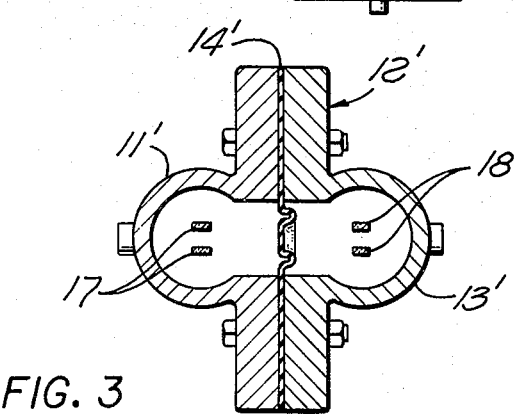
FIG. 3 is a transverse sectional view of the gravitometer taken on the line 3—3 shown in FIG. 2.

The chambers have amorphous quartz tuning forks 17 and 18 with quartz stems and temperature sensors 19 and 20. See FIGS. 2 and 3.

Figure 4:
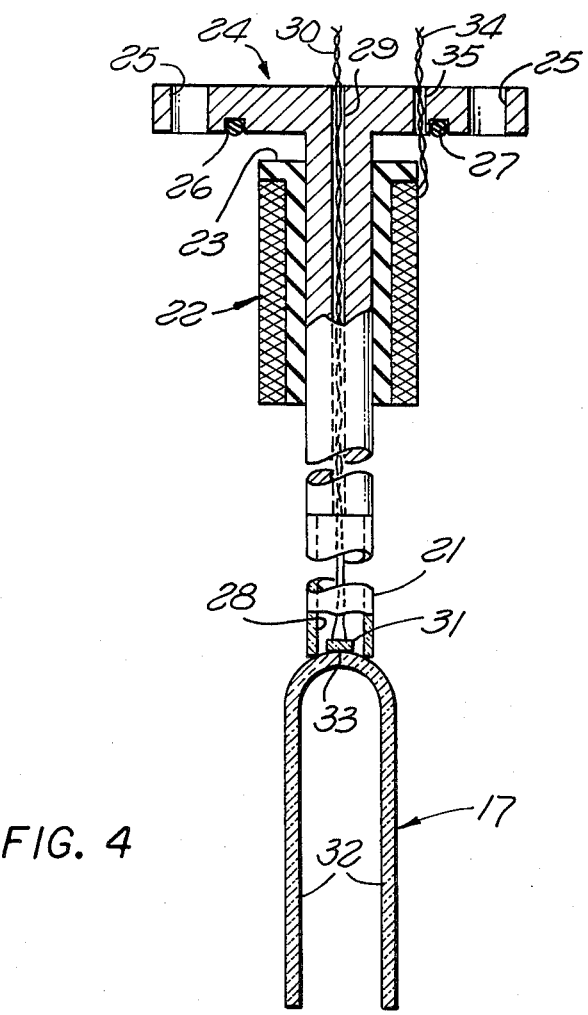
FIG. 4 is a vertical sectional view of a portion of the gravitometer taken on the line 4—4 shown in FIG. 2.

In FIG. 4, tuning fork 17 is fixed to a magnetostrictive post 21 having a drive coil 22 therearound wound on a spool 23. Post 21 is fixed to a base 24.

Base 24 has cap screw holes 25 so that base 24 may be fixed to cylinder 11'. Base 24 also has an O-ring groove 26 and an O-ring 27 therein.

Passageways 28 and 29 are provided through post 21 and base 24 for lead wires 30 from a piezoelectric crystal 31.

Fork 17 has legs 32 and a bight portion 33 to which crystal 31 is fixed.

Coil 22 has leads 34 which extend through a conventional sealed passageway 35.

The arrangement of fork 18 (FIG. 2) may be identical to that shown in FIG. 4, if desired.

Figure 5:
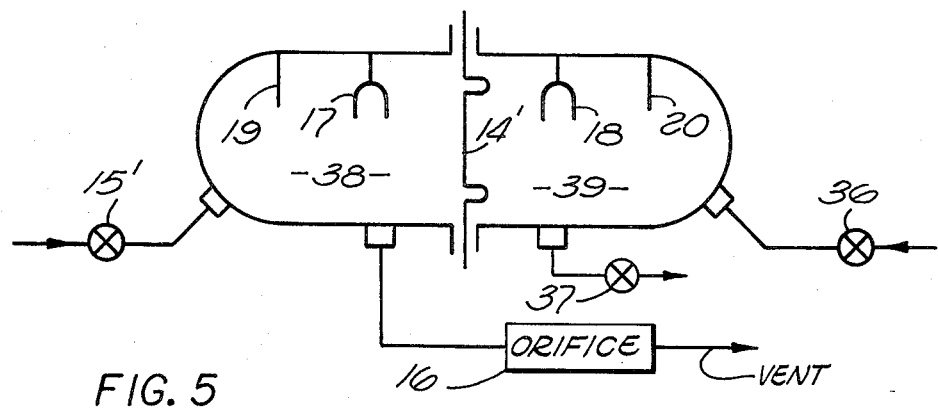
FIG. 5 is a schematic diagram of the gravitometer shown in FIGS. 1-4.

FIG. 5 is a diagrammatic of FIG. 2 and includes sensors 19 and 20, forks 17 and 18, gas valve 15', an air charging needle valve 36, a check valve 37, orifice 16 and diaphragm 14'. Chambers 38 and 39 are sealed except as described herein. Diaphragm 14' keeps the pressure in chamber 38 equal to that in chamber 39, and vice versa.

Figure 6:
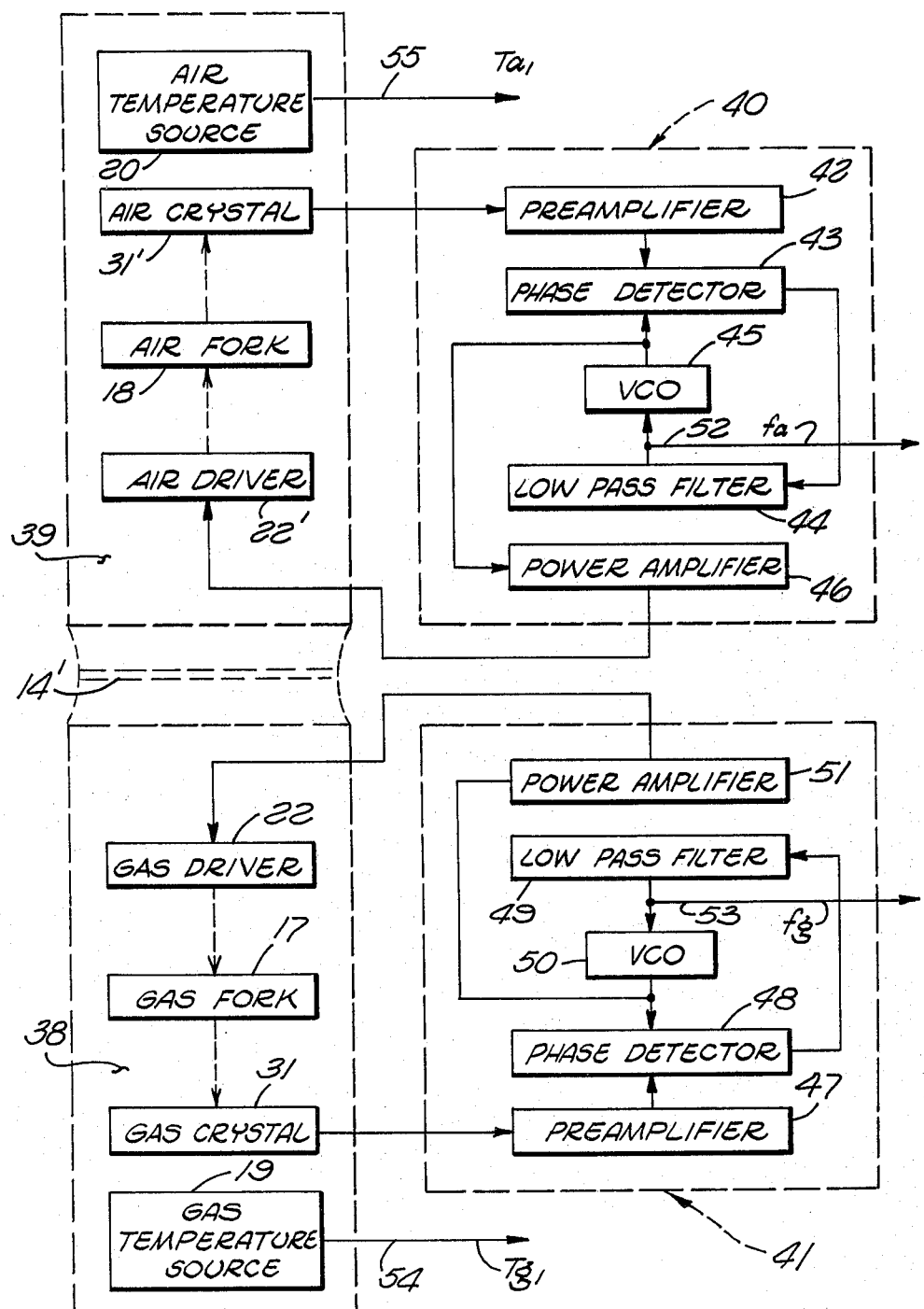
FIG. 6 is a schematic diagram of a portion of the gravitometer shown in FIGS. 1-5.

Forks 17 and 18 are vibrated. They form parts of two electromechanical oscillators as shown in FIG. 6. The contents of chamber 38 shown in FIG. 6 has already been described. The contents of chamber 39 in FIG. 6 may, if desired, be identical to that shown in chamber 38 in FIG. 6. In chamber 39 an air driver or coil 22' is provided to vibrate fork 18. Fork 18, in turn, has a crystal 31' which may be identical to crystal 31.

Essentially identical conventional phase locked loops are provided at 40 and 41 in FIG. 6, if desired. Phase locked loop 40 has a preamplifier 42, a phase detector 43, a low pass filter 44, a voltage controlled oscillator (VCO) 45, and a power amplifier 46 connected from crystal 31' to driver 22'. Alternatively, phase locked loops 40 and 41 may be conventional divider operated frequency multipliers.

Similarly, phase locked loop 41 has a preamplifier 47, a phase detector 48, a low pass filter 49, a VCO 50 and a power amplifier 51.

Loops 40 and 41 have output leads 52 and 53, respectively, that have signals thereon of frequencies $f_a$ and $f_g$, respectively.

Sources 19 and 20 have signals $T_{gl}$ and $T_{al}$ on output leads 54 and 55, respectively, proportional to the temperatures (e.g. in Farenheit or Centigrade) in chambers 38 and 39, respectively.

The density of air in chamber 39 (FIG. 5) is $D_a$ defined thus:

$$D_a = \frac{A_a}{f_a^2} - B_a \tag{1}$$

Where $A_a$ and $B_a$ include values related to compressibility $z_a$ and gas constant $R_a$. $A_a$ and $B_a$ are, by calibration, derived from the known equation:

$$PV = MZRT \tag{2}$$

where

P is absolute pressure,
V is volume,
M is mass,
R is the gas constant,
T is absolute temperature and
Z is compressibility.

$A_a$ and $B_a$ are constants derived empirically in a known way described in U.S. Pat. No. 3,677,067 issued July 18, 1972.

Similarly, the density $D_g$ of the gas in chamber 38 is:

$$D_g = \frac{A_g}{f_g^2} - B_g \tag{3}$$

where $A_g$ and $B_g$ are constants derived in the same way.

In the special case of chambers 38 and 39, and diaphragm 14', the pressures in chambers 38 and 39 are equal because diaphragm 14' is flexible, elastic or rubber or the like.

If $T_g = T_{gl} + T_o \tag{4}$ and $T_a = T_{al} + T_o \tag{5}$ from (1) and (3), gravity G is:

$$G = \frac{D_g(T_{gl} + T_o)}{D_a(T_{al} + T_o)} \tag{6}$$

or $$G = \frac{\left[\dfrac{A_g}{f_g^2} - B_g\right][T_{gl} + T_o]}{\left[\dfrac{A_a}{f_a^2} - B_a\right][T_{al} + T_o]} \tag{7}$$

where temperatures $T_{gl}$ and $T_{al}$ are sensed at 19 and 20 in FIG. 5, respectively.

Figure 7:
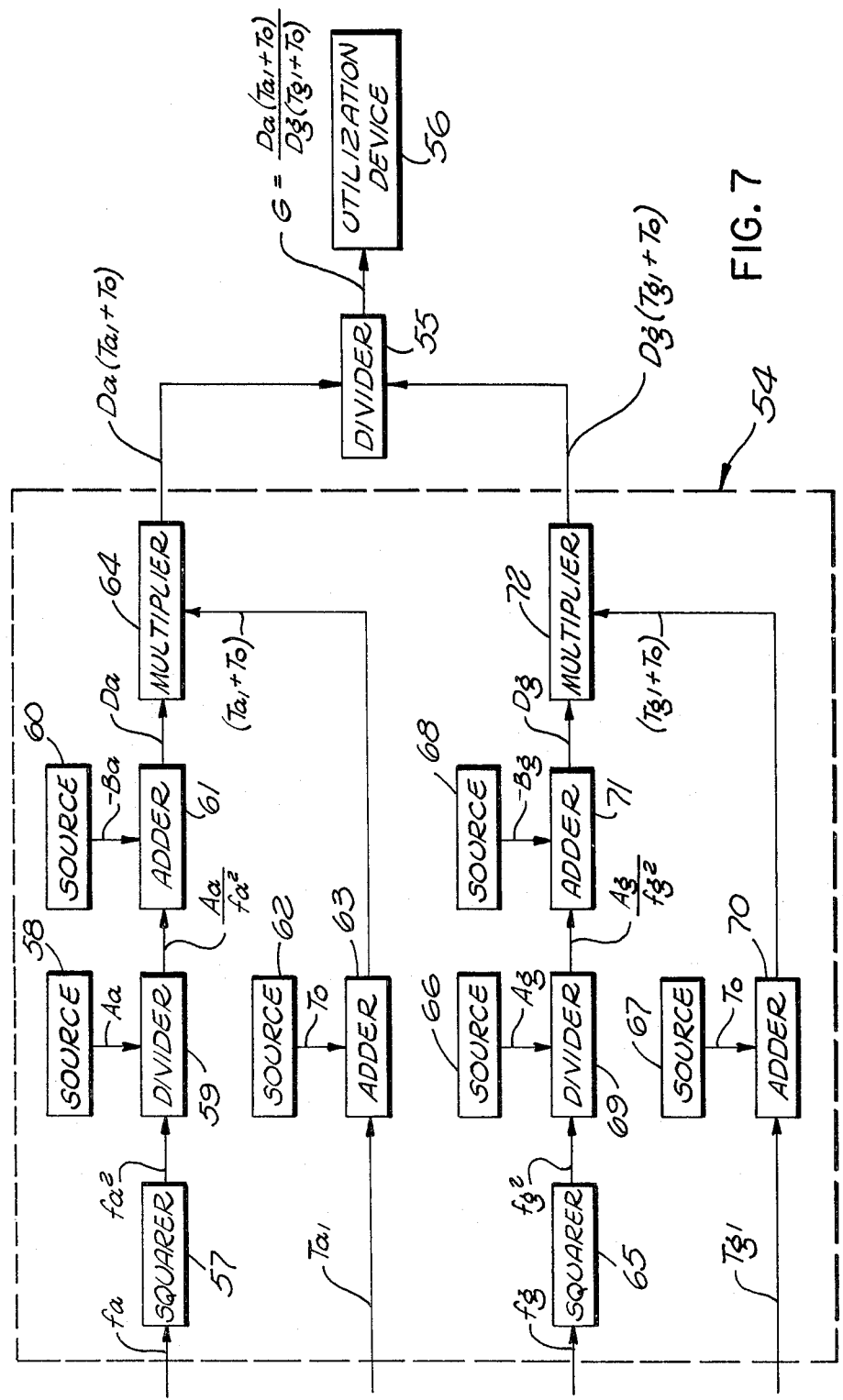
FIG. 7 is a block diagram of a gravity computer for use with the gravitometer of FIGS. 1-6.

Apparatus shown in FIG. 7 is an analog (but may be digital) computer that computes gravity according to equation (6).

In FIG. 7, inputs $D_a(T_{al}+T_o)$ and $D_b(T_{gl}+T_o)$ are supplied from a computer 54 to a divider 55 connected to a utilization device 56, which may be an indicator.

Computer 54 develops $D_a(T_{al}+T_o)$ by squaring $f_a$ at squarer 57, developing $A_a/f_a^2$ by source 58 and divider 59, then developing (1) equal to $D_a$ with the use of source 60 and adder 61 (all analog adders may be adders or substractors because subtraction merely requires a negative, positive, reverse voltage or otherwise).

The output of adder 61 is then $D_a$. The term $(T_{al}+T_o)$ is developed by source 62 and adder 63. The output of adder 63 is multiplied by $D_a$ by multiplier 64.

The term $D_a(T_{gl}+T_o)$ is computed in exactly the same way as $D_a(T_{al}+T_o)$ by the use of squarer 65, sources 66, 67 and 68, divider 69, adders 70 and 71, and multiplier 72.

Figure 8:
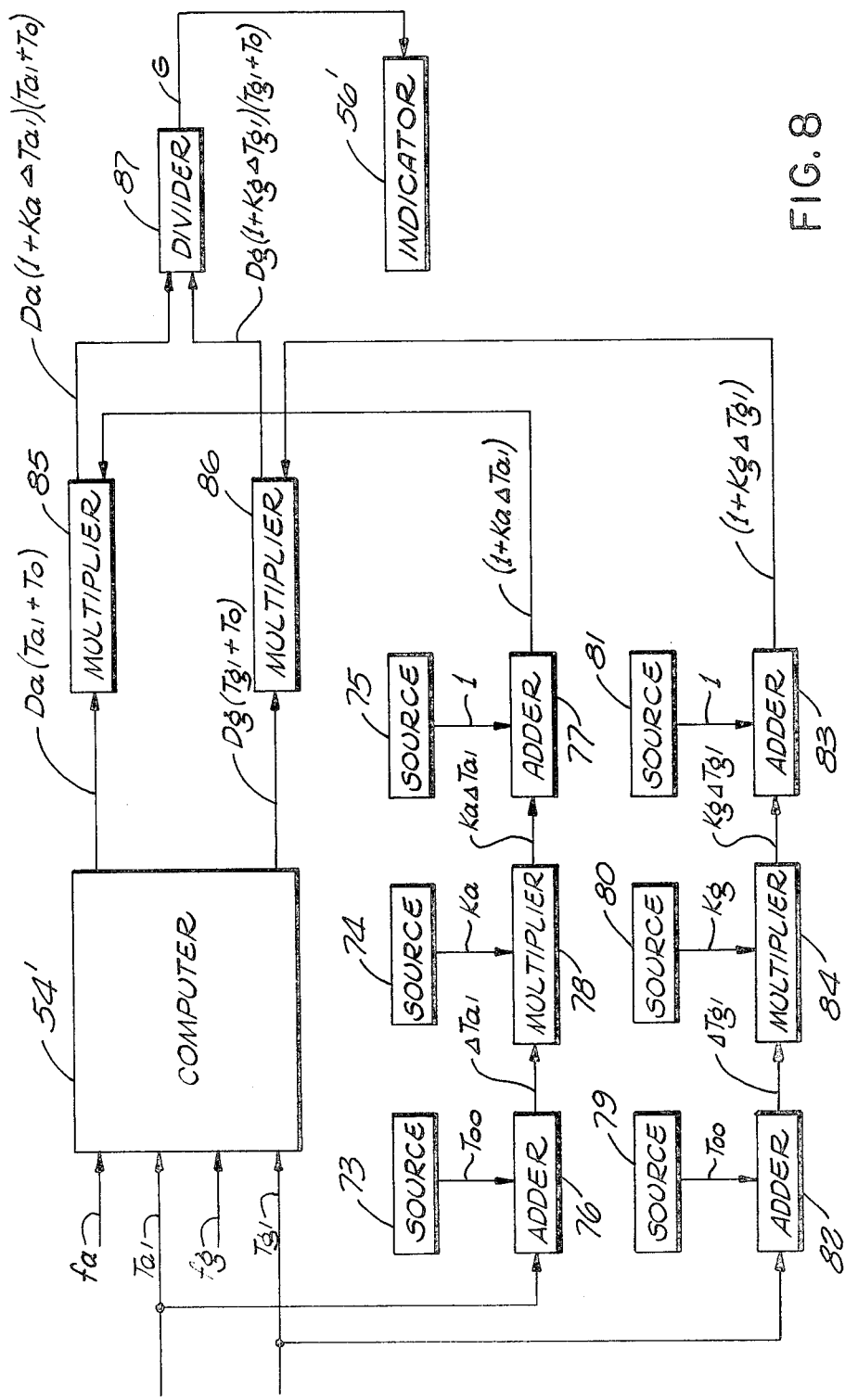
FIG. 8 is a block diagram of an alternative embodiment of a gravity computer constructed in accordance with the present invention.

In FIG. 8, a correction is made for the temperature sensitivities of $D_a$ and $D_g$. Computer 54' may be identical to computer 54. Sources 73, 74, and 75, adders 76 and 77, and multiplier 78 develop the term $(1+K_a\Delta T_{al})$ where $K_a$ is the thermal coefficient of air density and $\Delta T_{al}$ is the change in temperature from a known reference temperature at which the density error is zero (e.g. zero degrees F. or zero degrees C.).

The term $(1+K_g\Delta T_{gl})$ is developed exactly the same way through the use of sources 79, 80 and 81, adders 82 and 83, and multiplier 84.

A multiplier 85 produces a signal directly proportional to:

$$D_a(1+K_a\Delta T_{al})(T_{al}+T_o) \tag{8}$$

A multiplier 86 produces a signal directly proportional to:

$$D_g(1+K_g\Delta T_{gl})(T_{gl}+T_o) \tag{9}$$

Term (9) is divided by term (8) in a divider 87 to give G.

In any embodiment of the present invention, whether or not described herein, computations may all be or in part be performed by analog or digital computers. Signals $f_a$ and $f_g$ are in digital form to begin with and digital computers may be employed, if desired.

An indicator 56' may be employed the same as or different from device 56 (FIG. 7). Further, device 56 may be any indicator or may be a process controller or otherwise. The same is true of any utilization or other device disclosed herein.

Figures 9, 10:
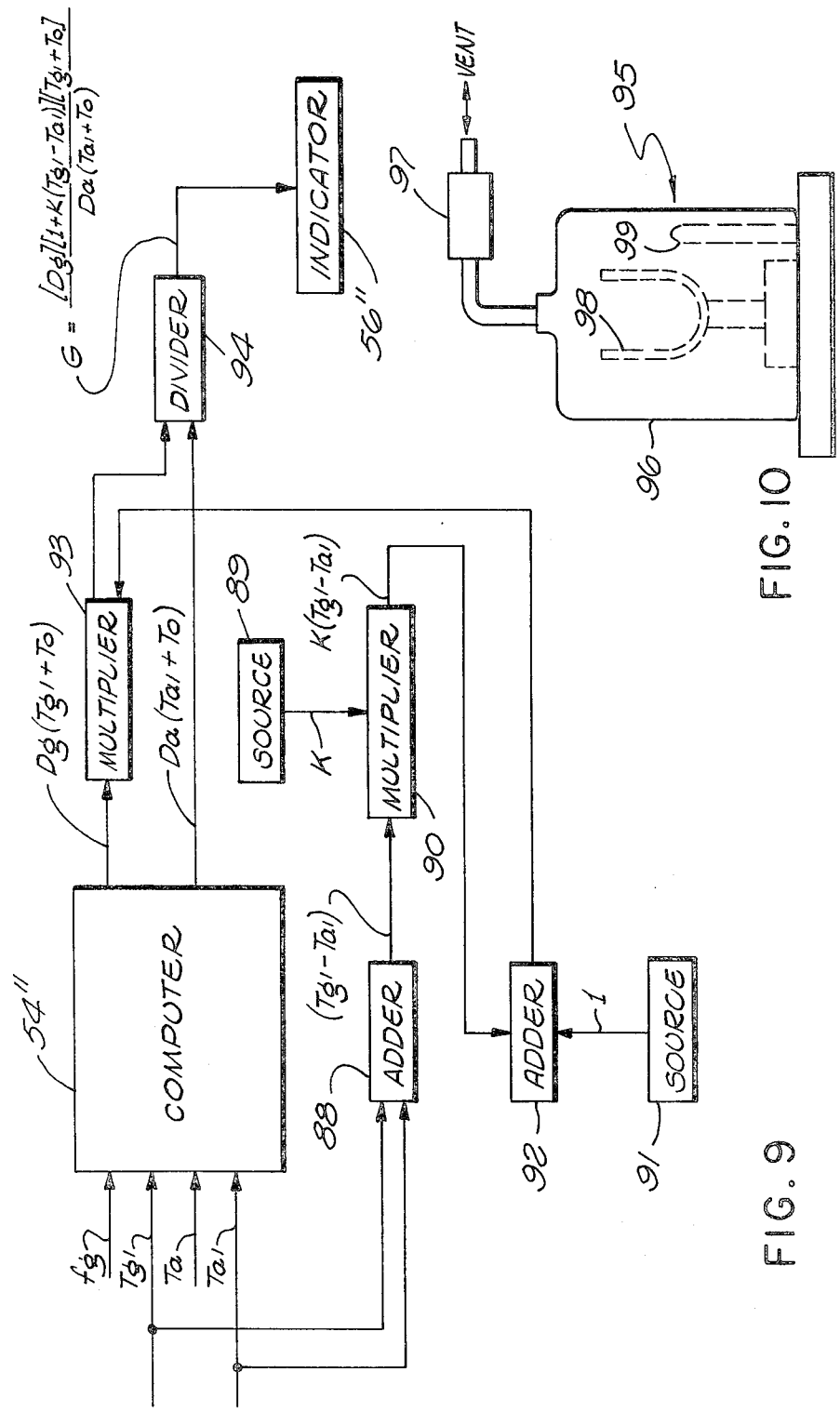
FIG. 9 is a block diagram of a second alternative embodiment of a gravity computer constructed in accordance with the present invention.
FIG. 10 is a side elevational view of a structure which may be employed in accordance with the present invention in a barometer or an altimeter.

In FIG. 9, computer 54'' may be identical to computer 54', if desired. Indicator 56'' may also be identical to indicator 56'. The embodiment of FIG. 9 can correct for errors in densities $D_g$ and $D_a$ due to changes in temperature.

If $T_{ro}$ is a reference temperature:

$$\Delta T_{al} = T_{al} - T_{ro} \tag{10}$$

$$\Delta T_{gl} = T_{gl} - T_{ro} \tag{11}$$

from FIG. 8:

$$G = \frac{D_g(1 + K_g\Delta T_{gl})(T_{gl} + T_g)}{D_a(1 + K_a\Delta T_{al})(T_{al} + T_o)} \tag{12}$$

However, if, as they usually do:

$$K_a\Delta T_{al} << 1 \tag{13}$$

$$K_a\Delta T_{gl} << 1 \tag{14}$$

and it is possible $$K_a = K_g = K \tag{15}$$

then, combining (11), (12) and (13)

$$G = \frac{\left[\frac{A_g}{f_g^2} - B_g\right] [1 + K(T_{gl} - T_{al})] [T_{gl} + T_o]}{\left[\frac{A_a}{f_a^2} - B_a\right] [T_{al} + T_o]} \quad (16)$$

The arrangement of FIG. 9 calculates gravity according to (16).

Computer 54″ computes $D_g$ $(T_{gl}+T_o)$ and $D_a$ $(T_{al}+T_o)$.

The adder 88 produces $(T_{gl}-T_{al})$. Source 89 and multiplier 90 develop $K(T_{gl}-T_{al})$.

Source 91 and adder 92 develop $[1+K(T_{gl}-T_{al})]$.

Multiplier 93 develops:

$$[D_g][1+K(T_{gl}-T_{al})][T_{gl}+T_o] \quad (17)$$

Divider 94 develops G according to equation (16).

A device 95 is shown in FIG. 10 which may be employed in a barometer or altimeter. A bell jar 96 or the like is hermetically sealed except that it is vented through a desiccator 97 to the atmosphere. An amorphous or other quartz tuning fork is shown at 98 with a temperature sensor 99. Fork 98 is vibrated as before.

In FIG. 11, the barometric system is shown including chamber 96, a squarer 100, a divider 101, and an adder 102 connected in that order to a multiplier 103. Sources 104 and 105 are connected to divider 101 and adder 102, respectively. Phase locked loop 100′ may be of the type shown in FIG. 6 at 40 or 41.

Temperature signal $T_p$ is impressed upon adder 106 and thence through multiplier 107 and adder 108 to multiplier 103.

Sources 106′, 109 and 110 are connected to multiplier 107 and 108, respectively.

Temperature signal $T_p$ proportional to the temperature inside bell jar 96 is also supplied to multiplier 103 through an adder 111.

Source 112 is connected to adder 111.

The pressure $P_p$ in chamber 96 is then computed in FIG. 11 thus:

$$P_p = \left[\frac{A_p}{f_p^2} - B_p\right] [1 + K_p \Delta T_p][T_p + T_o][Z] \quad (18)$$

where $D_p$ is equal to density, i.e.

$$D_p = \frac{A_p}{f_p^2} - B_p$$

$A_p$, $B_p$ and $K_p$ are constants,
$T_p$ is a change in temperature,
$(T_p+T_o)$ is absolute temperature, and
Z is the supercompressibility of air.

An indicator 113 is connected from multiplier 103.

An indicator 114 in FIG. 12 utilizes output signal $P_p$ in FIG. 11 to produce altitude y in an altimeter.

Circuits 115 and 116 are natural or Napierian logarithmic function generators.

Source 117 produces a constant output $P_o$ of a reference altitude pressure (e.g. sealevel).

Adder 118 adds as a subtractor to give:

$$\ln \frac{P_o}{P_p} \quad (19)$$

from inputs: $\ln P_p$ (20)

and:

$$\ln P_o \quad (21)$$

Source 119 produces constants:

$$\frac{P_o}{D_o g} \quad (22)$$

where
$D_o$ is a constant reference density, and
g is acceleration due to gravity.

Thus from FIG. 12, $$y = \frac{P_o}{gD_o} \ln \frac{P_o}{P_p} \quad (23)$$

where $P_p$ is defined in (18).

Figures 13, 14:
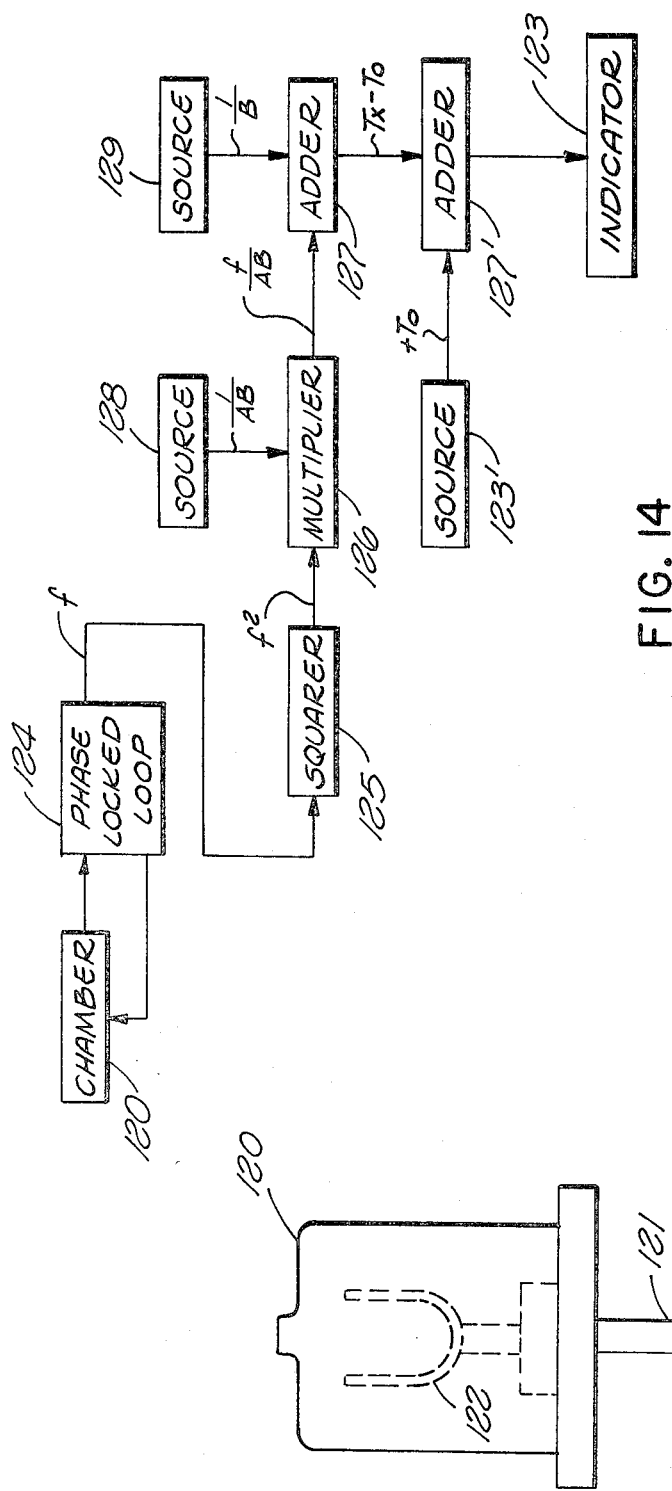
FIG. 13 is a side elevation view of temperature sensitive apparatus constructed in accordance with the present invention.
FIG. 14 is a block diagram of a temperature computer constructed in accordance with the present invention.

An air-tight bell jar having a vacuum therein is shown at 120 in FIG. 13. A member 121 provides a conductive path to a quartz tuning fork 122, whereby temperature may be detected and/or indicated.

One temperature indicator is shown at 123 in FIG. 14. Chamber 120 is connected thereto via phase locked loop 124, a squarer 125, a multiplier 126, an adder 127, and an adder 127′. Sources 128, 129 and 123′ are connected to multiplier 126, adder 127 and adder 127′.

The system of FIG. 14 computes temperature $T_x$ as where:

$$T_x = \frac{f^2 - A}{AB} + T_o \quad (24)$$

A and B are constants.

Phase locked loops 40 and 41 in FIG. 6 may be converted to frequency multipliers by the additions of dividers as is well known.

The phrase "computer means" is hereby defined for use herein and in the claims to include either analog or digital computer means, the same being equivalent for use herein.

In FIG. 13, $$f^2 = \frac{(3.89)^2 (8bt^3)(E)(1 + K_e \Delta T)}{12WL^3(1 + K_L \Delta T)^3} \quad (25)$$

where
f is frequency,
($bt^3/12$) is the moment of inertia of a fork leg,
E is Young's modulus,
$K_e$ is the temperature coefficient of the modulus,
$K_L$ is the temperature coefficient of the fork leg length, $$\Delta T_x = T_x - T_o \quad (26)$$

W is leg width,
L is leg length.

If $3K_L\Delta T << 1$ (27)

and:

$K_c\Delta T << 1$ (28)

then:

$(1+K_L\Delta T_x)^3 \approx (1+3K_L\Delta T_x)$ (29)

Thus:

$f^2 = A(1+B\Delta T_x)$ (30)

where $A = \dfrac{10.09 bt^3 E}{WL^3}$ (31)

Equation (29) from (26) and (27) may be written:

$B = K_c - 3K_n$ (32)

and:

$\Delta T_x = \dfrac{f^2 - A}{AB}$ (33)

$T_x - T_o = \dfrac{f^2 - A}{AB}$ (34)

$T_x = \dfrac{f^2 - A}{AB} + T_o$ (35)

All constants A, B and K with any one or more subscripts may be determined by an empirical calibration.

The general form of density D, with constants and variables of any subscripts is:

$D = \dfrac{A}{f^2} - B$ (36)

where:
f is directly proportional to the frequency of vibration of the tuning fork, and
A and B are empirically derived constants.
In prior equations, $K_o$ may be defined as:

$K_o = K_e - 3K_1$ (37).

The words or equivalents of "fork immersed in a fluid" is hereby defined for use herein and in the claims to mean "immersed in a gas or immersed in a liquid."

What is claimed is:

1. A vibration instrument comprising: a base; a housing sealed to said base to define a first space; vibratable tuning fork means in said first space including two substantially parallel legs connected at one pair of mutually adjacent ends by a bight portion, said tuning fork means having a variable frequency of vibration f; a longitudinal magnetostrictive member having first and second opposite ends on an axis fixed relative to said base and said bight portion, respectively, said parallel legs extending in a direction from said bight portion away from the said second end of said member in positions approximately symmetrical about said axis; a piezoelectric crystal fixed relative to said bight portion to produce an output signal of said frequency f equal to the said vibrational frequency of said tuning fork means; first driver means including a first driver coil mounted around said member, said first driver means also including an amplifier connected from said crystal to impress a signal upon said first driver coil of the same said frequency f to cause said tuning fork means to vibrate at said frequency f, said first driver means having an output at which an output signal is produced, said output signal having said frequency f; and first computer means connected to receive said crystal output signal for producing an output signal directly proportional to the first expression:

$\dfrac{A_g}{f_g^2} - B_g$ where $f_g = f$, and $A_g$ and $B_g$ are constants, said constants $A_g$ and $B_g$ having first and second sources, respectively, to provide first and second signals, respectively, to said first computer means directly proportional to said constants $A_g$ and $B_g$, respectively, and where the said first expression is directly proportional to the density of a fluid in which said vibratable tuning form means is immersed.

2. The invention as defined in claim 1, wherein a second base, a second housing, second tuning fork means, a second member, a second driver coil, a second piezoelectric crystal, second driver means and second computer means are provided to produce an output signal of a frequency $f_a$ corresponding to frequency $f_g$, said second base and said second housing defining a second space, a flexible diaphragm forming a common wall between said spaces to keep fluids therein at the same pressure, a temperature sensor in each of said first and second spaces such that the temperatures sensed in said spaces are $T_{al}$ and $T_{gl}$ where $T_{al}$ is the temperature in said second space, and $T_{gl}$ is the temperature in said first space, and third computer means connected from the outputs of said first and second computer means for producing an output signal directly proportional to the gravity G of a gas of interest, said gas of interest occupying said first space, air occupying said second space, said second computer means producing an output signal proportional to the second expression:

$\dfrac{A_a}{f_a^2} - B_a$ where $A_a$ and $B_a$ are constants, and where the said second expression is directly proportional to the density of air in said second space in which said second vibratable tuning fork means is located, said third computer means producing an output directly proportional to G, where $G = \dfrac{\left[\dfrac{A_g}{f_g^2} - B_g\right]}{\left[\dfrac{A_a}{f_a^2} - B_a\right]} \cdot \dfrac{[T_{g1} + T_o]}{[T_{a1} + T_o]}$ where $A_g$, $B_g$, $A_a$, $B_a$ and $T_o$ are constants,
$[T_{gl} + T_o]$ is the absolute temperature in said first space, and $[T_{al} + T_o]$ is the absolute temperature in said second space, second, third, fourth and fifth sources to provide output signals directly proportional to $A_a$, $B_a$, $[T_{gl}+T_o]$ and $[T_{al}+T_o]$, respectively, said fourth and fifth sources impressing said output signals thereof on said third computer means, said second and third sources impressing said output signals thereof on said second computer means.

3. The invention as defined in claim 1, wherein a second base, a second housing, second tuning fork means, a second member, a second driver coil, a second piezoelectric crystal, second driver means and second computer means are provided to produce an output signal of frequency $f_a$ corresponding to frequency $f_g$, said second base and said second housing defining a second space, a flexible diaphragm forming a common wall between said spaces to keep fluids therein at the same pressure, a temperature sensor in each of said first and second spaces such that the temperatures sensed in said spaces are $T_{al}$ and $T_{gl}$ where $T_{al}$ is the temperature in said second space, and $T_{gl}$ is the temperature in said first space, and third computer means connected from the outputs of said first and second computer means, respectively, for producing an output signal directly proportional to the gravity G of a gas of interest, said gas of interest occupying said first space, air occupying said second space, said second computer means producing an output signal proportional to the second expression:

$$\frac{A_a}{f_a^2} - B_a$$

where $A_a$ and $B_a$ are constants, and where the said second expression is directly proportional to the density of air in said second space in which said second vibratable tuning fork means is located, said third computer means producing an output directly proportional to G, where:

$$G = \frac{\left[\dfrac{A_g}{f_g^2} - B_g\right]}{\left[\dfrac{A_a}{f_a^2} - B_a\right]} - \frac{[1 + K(T_{g1} - T_{a1})][T_{g1} + T_o]}{[T_{a1} + T_o]}$$

where $A_g$, $B_g$, $A_a$, $B_a$, K and $T_o$ are constants, $T_{gl}$ and $T_{al}$ are the temperatures in said first and second spaces, respectively, and $[T_{gl}+T_o]$ and $[T_{al}+T_o]$ are the absolute temperatures in said first and second spaces, respectively, third, fourth, fifth, sixth, seventh and eighth sources for producing output signals directly proportional to $A_a$, $B_a$, K, $T_o$, $T_{gl}$, $T_{al}$, $[T_{gl}+T_o]$ and $[T_{al}+T_o]$, respectively, said second and third sources impressing said output signals thereof on said second computer means, said fourth, fifth, sixth, seventh and eighth source output signals being impressed upon said third computer means.

4. The invention as defined in claim 1, wherein third sensor means are provided to produce an output signal proportional to the temperature $T_p$ in said first space, said first computer means being responsive to said third sensor means output signal to produce said first computer means output signal in direct proportion to the pressure $P_p$ in said space computed thus:

$$P_p = \left[\frac{A_p^2}{f_p^2} - B_p\right][1 + K_p \Delta T_p][T_p + T_o][Z]$$

where $A_p$ and $B_p$ are constants equal to $A_g$ and $B_g$, respectively, $\Delta T_p$ is the change in temperature in the space, $[T_p+T_o]$ is the absolute temperature in the space, $K_p$ is a constant, Z is the compressibility of air, and $f_p = f$, fourth, fifth and sixth sensors being provided to produce three respective output signals directly proportional to $K_p$, $T_o$, and Z, said fourth, fifth and sixth sensor output signals being impressed upon said first computer means.

5. The invention as defined in claim 4, wherein said pressure $P_p$ is barometric pressure, a desiccator being provided, said desiccator providing communnication from the atmosphere to said first space.

6. The invention as defined in claim 4, wherein second computer means are provided, said second computer means providing an altimeter reading, said second computer means being connected from said first computer means to receive said first computer means output signal and to be responsive thereto to produce an output signal in direct proportion to altitude y defined thus:

$$y = \frac{P_o}{gD_o} \ln \frac{P_o}{P_p}$$

where:
$P_o$ is atmospheric pressure at a reference altitude,
$D_o$ is the density of air at said reference altitude, and
g is acceleration due to the earth's gravity, seventh, eighth and ninth sensors being provided to produce output signals directly proportional to $P_o$, $D_o$ and g, respectively, said sensor output signals being impressed upon said second computer means.

7. The invention as defined in claim 1, wherein a second base, a second housing, second tuning fork means, a second member, a second driver coil, a second piezoelectric crystal, second driver means and second computer means are provided to produce an output signal of a frequency $f_a$ corresponding to frequency $f_g$, said second base and said second housing defining a second space, a flexible diaphragm forming a common wall between said spaces to keep fluids therein at the same pressure, a temperature sensor in each of said first and second spaces such that the temperatures sensed in said spaces are $T_{al}$ and $T_{gl}$ where $T_{al}$ is the temperature in said second space, and $T_{gl}$ is the temperature in said first space, and third computer means connected from the outputs of said first and second computer means for producing an output signal directly proportional to the gravity G of a gas of interest, said gas of interest occupying said first space, air occupying said second space, said second computer means producing an output signal proportional to the second expression:

$$\frac{A_a}{f_a^2} - B_a$$

where $A_a$ and $B_a$ are constants, and where the said second expression is directly proportional to the density of air in said second space in which said second vibratable tuning fork means is located, said third computer means producing an output directly proportional to G, where said third computer means computes the gravity G of said gas of interest thus:

$$G = \frac{\left[\dfrac{A_g}{f_g^2} - B_g\right][1 + K_g \Delta T_{g1}][T_{g1} + T_o]}{\left[\dfrac{A_a}{f_a^2} - B_a\right][1 + K_a \Delta T_{a1}][T_{a1} + T_o]}$$

where $A_a$, $B_a$, $K_g$ and $K_a$ are constants, $\Delta T_{gl}$ is the change in temperature in said first space, $\Delta T_{al}$ is the change in temperature in said second space, $[T_{gl}+T_o]$ is the absolute temperature in said first space, and $[T_{al}+T_o]$ is the absolute temperature in said second space, third, fourth, fifth, sixth, seventh and eighth sensors being provided to produce respective output signals directly proportional to $A_a$, $B_a$, $K_g$, $K_a$, $[T_{gl}+T_o]$ and $[T_{al}+T_o]$, respectively, said fifth, sixth, seventh and eighth sensor output signals being impressed upon said third computer means, said third and fourth sensor output signals being impressed upon said second computer means.

8. The invention as defined in claim 1, wherein said tuning fork means is made of quartz.

9. A gravitometer comprising: first means for providing a first enclosed space to hold air of a temperature $T_a$; second means for providing a second enclosed space to hold a gas of interest of a temperature $T_g$; first vibrator means in said first enclosed space having a member to vibrate at its resonant frequency $f_a$; second vibrator means in said second enclosed space having a member to vibrate at its resonant frequency $f_g$; means to cause the pressures in said first and second enclosed spaces to be equal; first and second sensors in said first and second enclosed spaces to produce output signals directly proportional to $T_a$ and $T_g$, respectively; first and second pick-offs connected from said first and second vibrator means to produce output signals of frequencies $f_a$ and $f_g$, respectively; computer means responsive to said first and second sensor output signals and both of said pick-off output signals for producing an output signal proportional to the gravity G of the gas in said second enclosed space.

10. The invention as defined in claim 9, wherein said computer means computes G thus;

$$G = \frac{\left[\dfrac{A_g}{f_g^2} - B_g\right][1 + K_g \Delta T_{g1}][T_{g1} + T_o]}{\left[\dfrac{A_a}{f_a^2} - B_a\right][1 + K_a \Delta T_{a1}][T_{a1} + T_o]}$$

where $A_g$, $B_g$, $A_a$, $B_a$, $K_g$, $K_a$ and $T_o$ are constants, $\Delta T_{gl}$ is the change in temperature in said second enclosed space, $\Delta T_{al}$ is the change in temperature in said first enclosed space, $[T_{gl}+T_o]$ is the absolute temperature in said enclosed space, and $[T_{al}+T_o]$ is the absolute temperature in said first enclosed space, third, fourth, fifth, sixth, seventh, eighth and ninth sensors being provided to produce output signals directly proportional to $A_g$, $B_g$, $A_a$, $B_a$, $K_g$, $K_a$ and $T_o$, respectively, said third, fourth, fifth, sixth, seventh, eighth and ninth sensor output signals being impressed upon said computer means.

11. The invention as defined in claim 9, wherein said computer means computes G thus:

$$G = \frac{\left[\dfrac{A_g}{f_g^2} - B_g\right][T_g + T_o][1 + K_o \Delta T]}{\left[\dfrac{A_a}{f_a^2} - B_a\right][T_a + T_o]}$$

where $A_g$, $B_g$, $A_a$, $B_a$ and $K_o$ are constants, $[T_a+T_o]$ is the absolute temperature in said first enclosed space, $[T_g+T_o]$ is the absolute temperature in said second enclosed space, and $\Delta T$ is the function of a change in temperature such that $1+K_o \Delta T$ corrects for what otherwise would be an error in the ratio:

$$\frac{\left[\dfrac{A_g}{f_g^2} - B_g\right]}{\left[\dfrac{A_a}{f_a^2} - B_a\right]}$$

third, fourth, fifth, sixth, seventh, eighth and ninth sensors for producing output signals directly proportional to $A_g$, $B_g$, $A_a$, $B_a$, $T_o$, $K_o$ and $\Delta T$, respectively, and impressing the same on said computer means.

12. A barometer comprising: chamber means for providing a partially enclosed space to hold air at a temperature of $T_p$; a first sensor for producing an output signal directly proportional to $T_p$; said chamber means having an opening therethrough to admit air from the atmosphere thereinto; vibrator means in said enclosed space having a member to vibrate at its resonant frequency $f_p$; a pick-off for producing an output signal of frequency $f_p$; and computer means connected to receive said first sensor output signal and said pick-off output signal for producing an output signal proportional to atmospheric pressure $P_p$.

13. The invention as defined in claim 12, wherein said computer means computes $P_p$ thus:

$$P_p = \left[\dfrac{A_p^2}{f_p^2} - B_p\right][1 + K_p \Delta T_p][T_p + T_o][Z]$$

where $A_p$, $B_p$ and $K_p$ are constants, $\Delta T_p$ is the change in temperature in said partially enclosed space, $[T_p+T_o]$ is the absolute temperature in said partially enclosed space, and Z is the compressibility of air, second, third, fourth, fifth, sixth and seventh sensors for producing output signals directly proportional to $A_p$, $B_p$, $K_p$, $\Delta T_p$, $T_o$ and Z, respectively, said second, third, fourth and seventh sensor output signals being connected to said computer means, said fifth sensor being connected from said first sensor to said computer means, the output signals of said first and sixth sensors being connected to said computer means.

14. An altimeter comprising: chamber means for providing a partially enclosed space to hold air at a temperature of $T_p$; a first sensor for producing an output signal directly proportional to $T_p$, said chamber means having an opening therethrough to admit air from the atmosphere thereinto; vibrator means in said enclosed space having a member to vibrate at its resonant frequency $f_p$; a pick-off for producing an output signal of a frequency equal to $f_p$; and computer means responsive to said first sensor and pick-off output signals for producing an output signal proportional to altitude y.

15. The invention as defined in claim 14, wherein y is computed thus:

$$y = \frac{P_o}{gD_o} \ln \frac{P_o}{P_p}$$

where $$P_p = \left[ \frac{A_p^2}{f_p^2} - B_p \right] [1 + K_p \Delta T_p][T_p + T_o][Z]$$

$P_o$, $D_o$, g, $A_p$, $B_p$ and $K_p$ are constants, $\Delta T_p$ is the change in temperature in said partially enclosed space, $[T_p+T_o]$ is the absolute temperature in said partially enclosed space, and Z is the compressibility of air, second, third, fourth, fifth, sixth, seventh, eighth and ninth sensors for producing output signals proportional to $P_o$, $D_o$, g, $A_p$, $B_p$, $K_p$, $T_o$ and Z, respectively, and for impressing the same upon said computer means.

16. Temperature sensitive apparatus comprising: enclosure means providing a sealed vacuum chamber; vibrator means in said vacuum chamber having a member to vibrate at its resonant frequency f; a pick-off for producing an output signal of said frequency f; means to provide a heat conductive path mounted through said enclosure means extending to a position in contact with said member; and computer means connected to receive said pick-off for producing an output signal directly proportional to the temperature $T_x$ of said member.

17. The invention as defined in claim 16, wherein said computer means produces an output signal directly proportional to said temperature $T_x$ where:

$$T_x = \frac{f^2 - A}{AB} + T_o$$

$T_o$ is a reference temperature, and A and B are constants.

* * * * *